US010123693B2

(12) United States Patent
Bex et al.

(10) Patent No.: US 10,123,693 B2
(45) Date of Patent: Nov. 13, 2018

(54) QUANTIFICATION OF INTER-OCULAR SUPPRESSION IN BINOCULAR VISION IMPAIRMENT

(71) Applicant: The Schepens Eye Research Institute, Inc., Boston, MA (US)

(72) Inventors: Peter Bex, Concord, MA (US); Steven Dakin, Auckland (NZ); MiYoung Kwon, Birmingham, AL (US); Emily Wiecek, Boston, MA (US)

( * ) Notice: Subject to any disclaimer, the term of this patent is extended or adjusted under 35 U.S.C. 154(b) by 0 days.

(21) Appl. No.: 15/312,376

(22) PCT Filed: Jul. 17, 2015

(86) PCT No.: PCT/US2015/041033
§ 371 (c)(1),
(2) Date: Nov. 18, 2016

(87) PCT Pub. No.: WO2016/022274
PCT Pub. Date: Feb. 11, 2016

(65) Prior Publication Data
US 2017/0079524 A1    Mar. 23, 2017

Related U.S. Application Data

(60) Provisional application No. 62/000,988, filed on May 20, 2014.

(51) Int. Cl.
*A61B 3/04* (2006.01)
*A61B 3/08* (2006.01)
(Continued)

(52) U.S. Cl.
CPC .............. *A61B 3/08* (2013.01); *A61B 3/032* (2013.01); *G02B 27/017* (2013.01);
(Continued)

(58) Field of Classification Search
CPC ....... A61B 3/032; A61B 3/028; A61B 3/0025; A61B 3/024
(Continued)

(56) References Cited

U.S. PATENT DOCUMENTS 5,206,671 A    4/1993  Eydelman et al.
7,367,675 B2 * 5/2008  Maddalena ............ A61B 3/028
                                                      351/237
(Continued)

FOREIGN PATENT DOCUMENTS

EP        0596617 A1    5/1994
JP     2010264281 A    11/2010
(Continued)

OTHER PUBLICATIONS

R. J. Babu, S. R. Clavagnier, W. R. Bobier, B. Thompson, and R. F. Hess, "The regional extent of suppression:strabismics vs non-strabismics," *IOVS*, vol. 54, pp. 6585-6593, Sep. 2013.
(Continued)

*Primary Examiner* — Mohammed Hasan
(74) *Attorney, Agent, or Firm* — Mintz Levin Cohn Ferris Glovsky and Popeo, P.C.

(57) ABSTRACT

Systems, apparatus, and methods are provided for quantifying inter-ocular suppression in binocular vision impairment. The systems, apparatus, and methods may include a stimulus presentation device and a controller which present different stimuli to each eye of a patient. The stimuli can include letters, numbers, or shapes which are arranged in rows, and columns with a stimulus presented to each eye in a location corresponding a stimulus presented to the other eye. The combined contrast of corresponding stimuli equals a predetermined value, and this contrast can be adjusted with each iteration of stimuli presented. This adjustment can be based upon the patient's reports of what is seen and adjust-
(Continued)

ments made by an algorithm executed by the controller. Suppression can thus be determined in terms of visual field location and quantified.

26 Claims, 9 Drawing Sheets

(51) Int. Cl.
 *A61B 3/032* (2006.01)
 *G02B 27/01* (2006.01)
(52) U.S. Cl.
 CPC .. *G02B 2027/011* (2013.01); *G02B 2027/014* (2013.01); *G02B 2027/0112* (2013.01); *G02B 2027/0134* (2013.01); *G02B 2027/0178* (2013.01)
(58) Field of Classification Search
 USPC ................................ 351/221, 222, 239–246
 See application file for complete search history.

(56) References Cited

U.S. PATENT DOCUMENTS

| | | | |
|---|---|---|---|
| 7,946,707 B1 | 5/2011 | McDonald, II et al. | |
| 2005/0079636 A1 | 4/2005 | White et al. | |
| 2006/0087618 A1* | 4/2006 | Smart ................ | A61B 3/005 351/222 |
| 2007/0200927 A1 | 8/2007 | Krenik | |
| 2007/0223213 A1 | 9/2007 | Bassi et al. | |
| 2009/0086166 A1 | 4/2009 | Kanazawa et al. | |
| 2010/0201942 A1* | 8/2010 | Hess .................. | A61B 3/022 351/201 |
| 2010/0283969 A1 | 11/2010 | Cooperstock et al. | |
| 2012/0320047 A1 | 12/2012 | Yanagita et al. | |
| 2013/0162944 A1 | 6/2013 | Fateh | |
| 2014/0085608 A1 | 3/2014 | Clopton | |
| 2015/0173613 A1* | 6/2015 | Gerrans .............. | A61B 3/14 351/206 |

FOREIGN PATENT DOCUMENTS

| | | |
|---|---|---|
| JP | 2012100756 A | 5/2012 |
| WO | WO-2013/170091 A1 | 11/2013 |

OTHER PUBLICATIONS

R. Asaoka, D. P. Crabb, T. Yamashita, R. A. Russell, Y. X. Wang, and D. F. Garway-Heath, "Patients Have Two Eyes!: Binocular versus Better Eye Visual Field Indices," *Invest. Ophthalmol. Vis. Sci.*, vol. 52, No. 9, pp. 7007-7011, 2011.

A. Jampolsky, "Characteristics of suppression in strabismus," *Arch. Ophthalmol.*, vol. 54, No. 5, p. 683, 1955.

E. Wiecek, S. C. Dakin, K. Lashkari, and P. J. Bex, "Qualitative and Quantitative Assessment of Metamorphopsia in Retinopathy Patients," in *ARVO*, 2013.

D. P. Crabb, N. D. Smith, F. C. Glen, R. Burton, and D. F. Garway-Heath, "How Does Glaucoma Look? Patient Perception of Visual Field Loss," Ophthalmology, vol. 120, No. 6, pp. 1120-1126, Jun. 2013.

J. A. Reche-Sainz, R. Gomez de Liaflo, N. Toledano-Fernandez, and J. García-Sánchez, "Binocular vision in glaucoma," *Arch. Soc. Esp. Ofialmol. Engl. Ed.*, vol. 88, No. 5, pp. 174-178, May 2013.

D. K. Newman and M. M. East, "Prevalence of amblyopia among defaulters of preschool vision screening," *Ophthalmic Epidemiol.*, vol. 7, No. 1, pp. 67-71, 2000.

B. Mansouri, B. Thompson, and R. F. Hess, "Measurement of suprathreshold binocular interactions in amblyopia," Vision Res., vol. 48, No. 28, pp. 2775-2784, Dec. 2008.

C.-B. Huang, J. Zhou, Z.-L. Lu, and Y. Zhou, "Deficient binocular combination reveals mechanisms of anisometropic amblyopia: signal attenuation and interocular inhibition," J. Vis., vol. 11, No. 6, 2011.

C. Owsley, "Contrast sensitivity," Ophthalmol. Clin. N. Am., vol. 16, No. 2, pp. 171-178, 2003.

L. Sloan, "Measurement of visual acuity," Ophthalmol. Rev., vol. 45, pp. 704-725, 1951.

F. W. Campbell and J. G. Robson, "Application of Fourier analysis to the visibility of gratings," J Physiol Lond, vol. 197, pp. 551-566, 1968.

I. Bailey and J. Lovie, "New design principles for visual acuity letter charts," Am. J. Optom. Physiol. Opt., vol. 53, pp. 740-745, 1976.

P. Asman and A. Heijl, "Evaluation of Methods for Automated Hemifield Analysis in Perimetry," *Arch. Ophthalmol.*, vol. 110, No. 6, pp. 820-826, Jun. 1992.

* cited by examiner

QUANTIFICATION OF INTER-OCULAR SUPPRESSION IN BINOCULAR VISION IMPAIRMENT

CROSS-REFERENCE TO RELATED APPLICATIONS

This application is a national phase entry of PCT patent application serial number PCT/US2015/041033, filed on Jul. 17, 2015, and entitled "QUANTIFICATION OF INTER-OCULAR SUPPRESSION IN BINOCULAR VISION IMPAIRMENT," which claims the benefit of U.S. provisional patent application Ser. No. 62/000,988, filed on May. 20, 2014, and entitled "QUANTIFICATION OF INTER-OCULAR SUPPRESSION IN BINOCULAR VISION IMPAIRMENT" which are incorporated by reference herein in their entireties.

GOVERNMENT LICENSE RIGHTS

This invention was made with government support under R01 EY021553 awarded by National Eye Institute of the U.S. National Institutes of Health. The government has certain rights in the invention.

FIELD

The subject matter described herein relates to systems, apparatus, and methods related to the assessment of the condition of a patient's vision, particularly for assessing the impairment of a patient's binocular vision.

BACKGROUND

Eye disease may cause asymmetric visual impairment in each eye. One eye of a patient may have better vision in one eye as a consequence of eye disease or a congenital disorder. The loss of vision in one of the patient's eye is often compensated for by healthy vision in the other eye for the same location. The better of the combined vision of the two visual fields for each eye, that is the monocular visual fields for each eye, makes up the binocular visual fields for a patient. Monocular visual impairment may be accompanied by suppression of the more impaired eye and dominance of the healthier eye. In current practice, the existence of suppression is usually identified, but may not be quantified with regard to the severity, by a clinician. Conditions in which suppression is often observed may include binocular misalignment conditions, anisometropic amblyopia, age-related macular degeneration (AMD), glaucoma, or the like. Binocular misalignment conditions may include strabismus, estropia, extropia, phoria, convergence insufficiency, and the like. Failure of suppression in such misalignment conditions may lead to diplopia, which is a condition in which two images of the same object appear in different locations. Alternatively, or additionally, failure of suppression in misalignment conditions may result in confusion, which is when images of different objects appear in the same location. Diplopia and confusion may also be present as a result of traumatic brain injury, as opposed to damage to a patient's eyes. To minimize the occurrence of confusion, diplopia, or both, a clinician may wish to encourage suppression. Current methods of encouraging suppression include the use of an occluder, such as an eye patch, to mask the image from one eye.

Amblyopia is an eye disorder commonly known as lazy eye and is the most common cause of monocular visual loss among children. Suppression is known to play a critical role in development of amblyopia. Thus, a reliable and timely assessment of suppression is believed to assist in detecting and treating amblyopia. The current methods of assessing suppression include the Worth 4 dot test, the use of Bagolini lenses, and OXO tests. However, none of the current clinical methods are able to quantify the level of suppression.

The Worth 4 dot test, is also known as the Worth Lights test. The Worth 4 dot test includes four circular lights presented to a patient in a diamond formation using a flashlight. Red-green anaglyphs are used to separate the images for each eye: the top red dot is presented to the right eye through the red filter, and two middle green dots are presented to the left eye through the green filter. A white dot at the bottom of the diamond is presented to both eyes. The bottom dot provides a fusional stimulus and is seen as yellow if neither eye is suppressed in that location. In cases where there is ocular dominance, or rivalrous alternation between the eyes, the bottom dot will be perceived as red or green by the patient. The patient is asked to report the number of dots he or she sees, the colors of the dots, and the relative positions of the dots at 40 cm near and 6 m far.

Bagolini lenses have fine striations that produce streaks when a flashlight is viewed by a patient. The clinician administering a test using Bagolini lenses places a first 45° lens over one eye and a second 135° lens over the other eye of the patient. That is to say, that first lens causes a stripe at a 45° angle to be seen by the eye it covers, and the second lens causes a stripe at 135° angle to be seen by the other eye, when the patient has normal binocular vision. When the patient sees only one stripe, then the patient is determined to have suppression of one eye.

The OXO test presents stripes, one above and one below the "X" of an OXO panel. The patient looks at the panel with both eyes, then each eye in turn while each eye is covered with polarizing lenses. The patient reports the number and locations of strips at 40 cm and 1.5 m distance.

SUMMARY

Methods, systems, and apparatus, including computer program products, are provided for quantification of inter-ocular suppression in binocular vision or a patient.

In some example embodiments, a system for quantifying suppression in binocular vision of a patient is disclosed. The system may include a stimuli presentation device and a controller. The stimuli presentation device may be configured to present stimuli that include a distinct stimulus for each eye of the patient. The controller is operably connected to the stimuli presentation device and may include a computer, an adaptive algorithm executed on the computer, and a stimulus generating component. The computer may include an interface configured to accept input from a clinician, a patient, or both. The adaptive algorithm may be configured to accept a report describing what the patient sees when presented with the stimuli and to calculate adjustments to the stimuli to be presented in the next iteration of stimuli. The stimulus generating component may be configured to provide the next iteration of stimuli to the patient via the stimuli presentation device.

The following features may be present in the system in any suitable combination. The stimuli presentation device may include 3D stereo shutter glasses, anaglyph glasses, polarized lenses, a Wheatstone stereogram, head mounted displays, lenticular screens, or any combination thereof. In some embodiments, the system may be configured to measure scale dependent suppression in the binocular vision of the patient. In some such embodiments, the stimuli may include bandpass filtered Sloan letters laid out in a manner comprising multiple rows of letters, each row of decreasing letter size, and each row having multiple letter, wherein each letter in a row is distinct and having a different amount of contrast. Additionally, each distinct stimulus for each eye of the patient may have the same number of rows of letters and columns of letters, in which a letter on a right eye stimulus corresponds to a letter on a left eye stimulus in a similar position, and the corresponding letters may have a combined contrast that is a fixed value. The Sloan letters of the stimuli may include peak spatial-frequencies of 0.5 to 10 cycles per degree in some embodiments. Alternatively, or additionally, the Sloan letters may create a pattern that covers a main area of a contrast sensitivity function in some embodiments. The system may be configured to measure suppression in the binocular vision of the patient while each eye of the patient is fixated on a spot on the distinct stimulus presented to each eye. In some embodiments, the system may be configured to measure both visual-field and spatial-frequency dependent suppression in the binocular vision of the patient. The stimuli may include numbers or colored dots in some embodiments of the system.

In a related aspect, in some example embodiments a method is disclosed that includes presenting stimuli to a patient, the stimuli comprising a distinct stimulus for each eye of the patient; accepting reports comprising observations from the patient regarding the stimuli; creating an adjusted stimuli via an adaptive algorithm executed on the computer controller, in which the adaptive algorithm uses the reports as input; and presenting to the patient the adjusted stimuli via a stimulus generating component of the computer controller and the stimuli presentation device. The stimulus presentation may be via a computer controller and a stimuli presentation device. The reports may be accepted via the computer controller.

The following features may be present in the method in any suitable combination. The method may further include evaluating the reports to determine whether suppression in binocular vision of the patient can be quantified. Additionally, the method may include quantifying suppression in binocular vision of the patient. The stimuli can include bandpass filtered Sloan letters, numbers, or colored dots in some embodiments. A stimulus for a right eye and a stimulus for a left eye may include corresponding features, and the features may include the bandpass filtered Sloan letters, numbers, or colored dots. In such embodiments, each feature may have a contrast value, in which a sum of the contrast values for corresponding features equals a fixed amount, and the fixed amount may be the same for each pair of corresponding features.

The above-noted aspects and features may be implemented in systems, apparatus, methods, and/or articles depending on the desired configuration. The details of one or more variations of the subject matter described herein are set forth in the accompanying drawings and the description below. Features and advantages of the subject matter described herein will be apparent from the description and drawings, and from the claims.

Figure 1A:
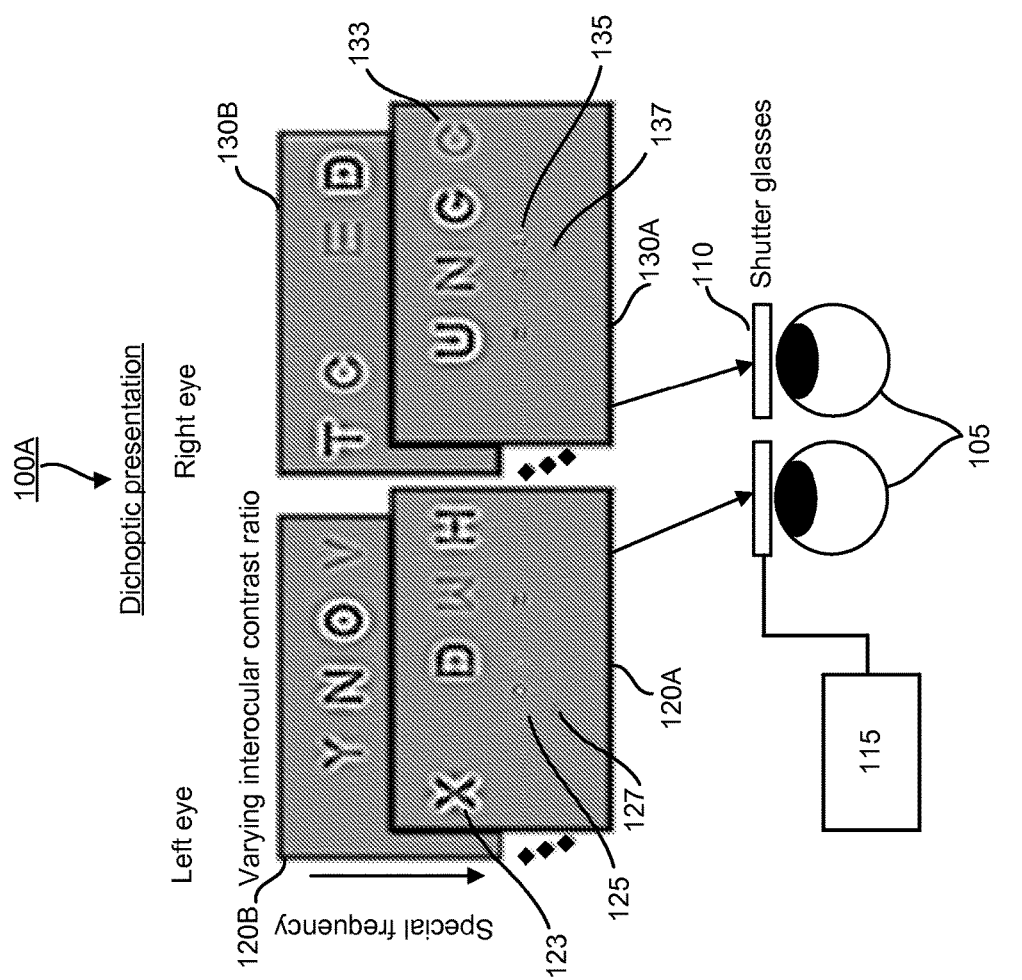
FIG. 1A depicts an example of a system for measuring suppression in the binocular vision of a patient, in accordance with some example embodiments.

Like labels are used to refer to same or similar items in the drawings.

DETAILED DESCRIPTION

Currently available clinical tests provide only a rough idea of presence of suppression. Although Bagolini test can be used to quantify the level of suppression by placing a neutral density bar in front of the non-suppressing eye until diplopia is reported by the patient, these results depend on the patient's subjective report of diplopia. Because of this drawback, it is rarely used. Furthermore, this tests only measure suppression in central vision and may not be easily modified to measure suppression outside the fovea.

In some example embodiments, there is provided apparatus, systems, and methods that provide quantification of inter-ocular suppression in binocular vision impairment. Without in any way limiting the claims, the apparatus, systems, and methods described herein may provide a sensitive, quantitative assessment of inter-ocular suppression. Some example embodiments may be capable of measuring the magnitude of suppression on a fine spatial scale, measuring the gradual changes in suppression, measuring foveal and/or peripheral vision that may be affected by central or peripheral eye disease, and/or measuring improvements in response to treatment of the eye with a greater degree of vision loss. Thus, these apparatus, systems, and methods can be used as a sensitive diagnostic tool, as well as provide an estimate of the efficacy of treatment outcomes, including surgical intervention to realign the patient's eyes, and approaches to overcome suppression or diplopia, such as traumatic brain injury therapies.

Interocular suppression may play a role in the etiology of amblyopia. While amblyopic vision often lacks excitatory binocular connections, such as binocular summation and stereopsis, the inhibitory nature of binocular interactions such as interocular suppression may remain persistent. This suppression may be associated with the severity of amblyopic deficits. When suppression is alleviated by equating the effective contrast of the two eyes (for example, binocularly balanced stimuli), some amblyopes may be able to achieve binocular fusion, which may promote excitatory binocular connections such as binocular summation. Treatment regimens designed to reduce suppression by promoting an exposure to binocularly balanced stimuli which may improve visual acuity and stereoacuity, while the residual and recurrent amblyopia may be attributed to remaining binocular imbalance. It may be possible to restore normal binocularity by addressing the imbalance in monocular signals. Consequently, assessment of interocular suppression may become increasingly important in both the detection and treatment of amblyopia.

Core amblyopic deficits such as contrast sensitivity loss and spatial distortion may exhibit spatial-frequency dependency. For example, contrast sensitivity loss in amblyopia may be more pronounced at mid-high spatial frequencies (SFs), while deficits at low spatial frequencies are less common. Similarly, perceptual distortion is more severe at higher spatial frequencies, with low spatial frequencies being essentially perceived veridically. In addition, gain control mechanisms may compensate for deficits at detection threshold. The distinction between threshold and suprathreshold contrast perception in amblyopia may raise questions concerning the spatial frequency dependence of interocular suppression. In some example embodiments, a quantitative, clinically-viable process for assessing suppression as a function of spatial frequency in amblyopia may be provided.

To assess the effect of spatial frequency on suppression, a series of dichoptic letter charts may be displayed to a patient in a test. FIG. 1A depicts a system including a series of dichoptic letter charts. In some example embodiments, the spatial frequency of Sloan letters may be bandpass filtered in a layout similar to the ETDRS acuity chart, which in this example includes four rows of decreasing letter size by five columns of varying letter contrast on a gray background. A different letter chart may be presented to each eye of an observer via stereo-shutter glasses. At each position, the identity and interocular contrast-ratio of the letter on each chart may differ while the spatial frequency content of the letter remains the same. The relative contrast of the letter in each eye may be adjusted across several charts to determine the balance point between the two eyes. The balance point may be defined as the interocular contrast-ratio required for a patient to see the letter in each eye with equal probability. In some example embodiments the foregoing test may take less than seven minutes.

FIG. 1A depicts an example of a system 100 including a series of dichoptic letter charts for measuring scale dependent suppression in the binocular vision of a patient. The system may include a stimuli presentation device 110 and a controller 115. The stimuli presentation device 110 may be 3D stereo shutter glasses, anaglyph glasses, polarized lenses, Wheatstone stereogram, head mounted displays, lenticular screens, or any other device that suitably presents different images to each eye. The controller 115 may be a computer that accepts input from the patient or clinician to present stimulus to the eyes of the patient 105 via a stimulus generating component. Each eye receives different stimulus 120A/B, 130A/B. As shown in FIG. 1A, the first stimulus for the left eye 120A and the first stimulus for the right eye 130A include bandpass filtered Sloan letters with peak spatial-frequencies of 0.5 to 10 cycles per degree. These patterns cover the main area of the contrast sensitivity function. The letters are laid out on a gray background, and the layout of the letters 123, 125, 127, 133, 135, 137 in the each stimulus is similar to the ETDRS acuity chart (i.e., the chart developed as part of the Early Treatment for Diabetic Retinopathy Study), with four rows of letters, each row of decreasing letter size, and each row having five letters. Each letter in a row has a different amount of contrast.

Each eye may be presented with a different stimulus via the stimuli presentation device 110, which in FIG. 1A is a pair of computer-controlled 3D stereo shutter glasses. At each position, the identity and inter-ocular contrast-ratio of the letter on each chart differs while the spatial-frequency content of the letter remains the same. The patient is instructed either by the clinician or the controller 115 to read aloud the chart in top-to-bottom and left-to-right order, reporting the identity of the letters, while using his or her foveal vision. No letters are repeated on each line, so the identity of each letter is unique, and in this way, suppression and diplopia can be detected from repetitions and confusions.

On each stimulus 120A/B, 130A/B, the combined contrast of both letters is fixed. That is to say, the sum of the contrast of the letter in the upper left-hand corner 123 of the chart for the left eye 120A and the letter in the upper left-hand corner 133 of the chart for the right eye 130A is the same as the sum of the first letters 125, 135 of the second rows and of the third row 127, 137. A patient with normal sight perceives the letter with higher contrast. When the effective contrast of the letter presented to each eye is balanced, each letter is reported with equal frequency. As the patient reports what he or she perceives, the controller 115 adjusts the inter-ocular contrast ratio to iteratively determine the presence and degree of suppression. For patients with normal vision, the balance point when the letter shown to the left eye and that shown to the right eye are perceived equally typically occurs when the inter-ocular contrast ratio is close to 0.5. Suppression is quantified as the contrast ratio at this balance point. As mentioned above, on successive charts, the interocular contrast ratios on each line are adaptively updated by an algorithm to determine the ratio at which the letter in each eye is reported with equal probability. This process yields the estimation of suppression for each spatial frequency. It may be after about 10 charts are read by the patient that a reliable estimate of suppression at multiple spatial frequencies is reached.

In some example embodiments, ten letters of the alphabet in Sloan font may be used by the system in FIG. 1A to measure suppression. Other fonts and numbers of letters may be used as well. Test letters may be spatially bandpass filtered with a cosine log filter with peak object spatial frequency of 3 cycles per letter (c/letter). The filter may have a bandwidth (full-width at half-height) of 1-octave and may be radially symmetrical in the log-frequency domain. In some example embodiments, the retinal spatial frequency of the test letters may range between 0.5 to 5 cycles per degree (c/deg) at a viewing distance of 57 cm. In some example embodiments, the retinal spatial frequency may be achieved by fixing the object spatial frequency at 3 cycles/letter and varying the image sizes determined by an angular size such as 0.6°, 1.2°, 2°, and 6°. Other angular sizes may be used as well. A spatial frequency of 3 c/letter may be in a rage of optimal spatial-frequency size between 1 and 7 c/letter depending on angular letter size.

Test letters may be displayed on a uniform gray background (60 cd/m$^2$) with varying contrasts such as Michelson contrasts. The stimuli may be generated and controlled by controller 115 that may include a computer. For example, a personal computer may control the stimuli. The personal computer may use software such as MATLAB that may include a psychophysics toolbox extension. Stimuli may be presented on a liquid crystal display monitor. For example, a computer display may be used such as an Asus VS278H-E having a refresh rate of 144 Hz and a resolution of 1920× 1080 and brightness of 250 cd/m². Stimuli may be rendered with grayscale levels using a bit-stealing method. The monitor may be calibrated using a spectrophotometer such as a Photo Research SpectraScan 655 and may be linearized. Stereo-shutter glasses may be used by patients/subjects. For example, nVidia Corp. stereo-shutter glasses may be used. In some example embodiments, stereo-shutter may have a frame rate 72 Hz per eye. Other frame rates may also be used.

As shown in FIG. 1A, the letters may be arranged in a layout similar to the ETDRS acuity chart with four rows of decreasing letter size and five columns of varying contrast. A different letter chart may be presented via stereo-shutter glasses to the weak eye compared to the strong eye. At each letter position on each chart, the identity and interocular contrast-ratio of the letter on each chart may differ while the spatial frequency content of the letter remains the same. The sum of the interocular contrast ratio across the two eyes may be fixed at 100% contrast or any other contrast value. For example, when using a 100% contrast value, the contrast in the weak eye may be 70%, and the contrast in the strong eye may be 30% or vice versa. To minimize participant confusion, the same letter may not appear twice in the same row. In some example embodiments, the interocular contrast ratio may be randomized across five letter slots in each row to avoid any ascending or descending pattern of contrast arrangement, which may potentially bias a participant's response.

Participants may read aloud the letters in the chart from top-to-bottom and left-to-right order as quickly and accurately as possible with unconstrained eye movements. In case participants experience binocular rivalry, they may be instructed to report the more dominant percept. Participants may be encouraged to report their percept as quickly as possible in order to minimize binocular rivalry. Their responses may be recorded. Completion of the first chart may cause a second chart that may be followed by subsequent charts. The relative contrast of the letter in each eye may be determined via an adaptive procedure. For example, for a given chart, the proportion of correct recognition may be determined at each interocular contrast ratio (each letter slot, 5 slots per line), which may be used to estimate the balance point (BP) between the two eyes for each spatial frequency (each line in the chart). The balance point may be defined as the interocular contrast-ratio yielding letter recognition in each eye with equal (50%) or nearly equal probability. The balance point may be updated after each letter chart based on the results from the most recent letter chart and the previously tested letter charts. The updated balance point may be used to determine the range of contrast ratios for a subsequent chart. In this way, over several charts, the range of interocular contrast-ratio may converge to a balance point. On successive letter charts, the testing points may be adjusted to be closer to the estimated balance point. The updating process may be an adaptive process. In some example embodiments, the balance points may be computed for each spatial frequency arranged in each row. In some example embodiments, participants may be given a one or more practice tests before a test to determine the balance point is performed. A testing session may last 7 minutes or less.

In some example embodiments consistent with FIG. 1A, letters that are bandpass filtered may be used as test stimuli. For example, letters in a Sloan font may be filtered to produce peak spatial-frequencies of 0.5 to 5 cycles per degree. Letters may be arranged in a layout similar to the ETDRS acuity chart including four rows of decreasing letter size by five columns of varying letter contrast on a gray background. Each row may contain a single spatial frequency of test letters such as 0.5, 1.5, 2.5, and 5.0 c/deg. Each slot may contain a different interocular contrast ratio. A different letter chart may be presented to each eye via stereo-shutter glasses. At each letter slot, the identity and interocular contrast-ratio of the letter on each chart may differ while the spatial-frequency content of the letter may remain the same. Participants may read the chart in left-to-right and top-to-bottom order. The relative contrast of the letter in each eye may be adjusted across several charts to determine the interocular balance point (BP). The balance point may be defined as the interocular contrast-ratio required for participants to report the letter in each eye with equal probability (0.5 proportion responses for the letter presented to the weak eye).

Figure 1B:
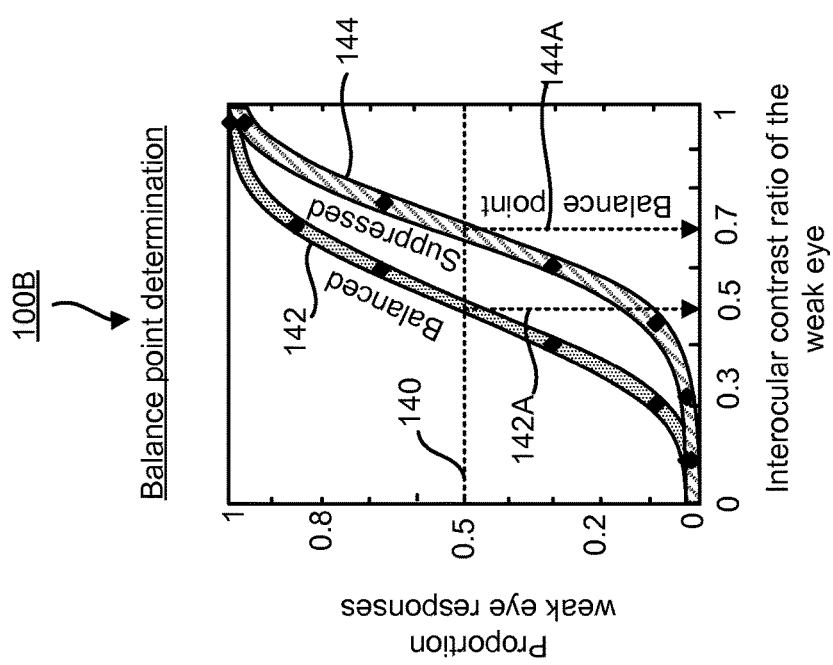
FIG. 1B depicts an example of a graph to determine a balance point, in accordance with some example embodiments.

FIG. 1B depicts a chart for determining a balance point, in accordance with some example embodiments. For example, a psychometric function may be used in in the determination of a balance point between the proportion of participant responses from a weak eye and an interocular contrast ratio of the weak eye. Data corresponding to the strong eye responses may be the mirror reversal of the data from the weak eye because the proportion of strong eye responses may equal one minus the proportion of weak eye responses. A test of a participant may determine the proportion of weak eye responses as a function of interocular contrast ratio. In some example embodiments, the resulting data may be fit to a Weibull function to derive a balance point yielding 50% identification for each eye. See, for example, the black dashed line 140 in FIG. 1B. Curves 142 and 144 represent proportions of weak eye responses as a function of interocular contrast ratio for different participants. Curve 142 represents data from a normally sighted patient/participant whose binocular vision is well balanced. As such, their balance point (x-axis value in FIG. 1B) is close to a value of 0.5 at 142A. In some example embodiments, the balance point may correspond to an interocular contrast ratio (x-axis in FIG. 1B) that corresponds to 50% of responses (y-axis in FIG. 1B) from the patient's weak eye. Curve 144 corresponds to a participant whose weak eye is suppressed, resulting in a balance point that is higher than 0.5. For example, FIG. 1B at 144A shows a participant with a balance point of approximately 0.7.

In some example embodiments, data containing a participant's letter recognition at varying contrast ratios may be collected in accordance with the foregoing. A balance point may be determined from the data by fitting the psychometric function to the data. Psychometric functions of percent correct versus interocular contrast ratio of the weak eye may be created by fitting the data with Weibull functions as shown in FIG. 1B. A curve fit may be determined for a participant using a search method. For example, a simplex search method may be used to minimize the weighted residual sum of squares. Other searches may also be used. In some example embodiments, the reciprocal of the variance of each data point ($1/\sigma^2$) may be used to weight in the curve fit. The balance point may be based on the estimated 50% correct point on the psychometric function for each spatial frequency. For example, the balance point of 0.5 may indicate 50% contrast in the weak eye matches 50% contrast in the strong eye (FIG. 1B at 142, 142A), suggesting that both eyes are well balanced. On the other hand, a balance point of 0.8 means that 80% contrast in the weak eye matches 20% contrast in the strong eye. Thus, the larger the balance point depicted in a rightward shift of the psychometric function, the more attenuated or suppressed the input signal of the weak eye may be. For example, a shift from curve 142 to curve 144 as shown in FIG. 1B.

Figure 2:
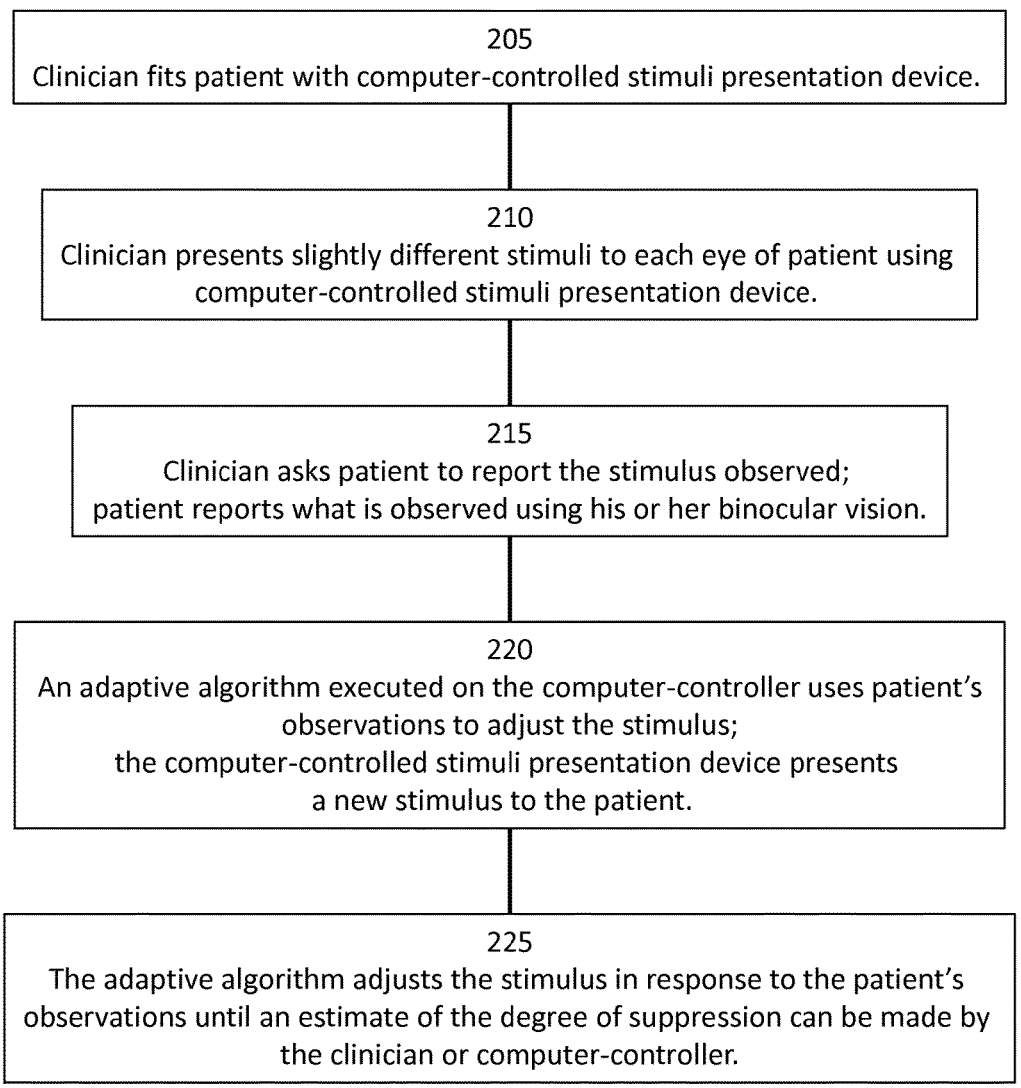
FIG. 2 depicts a block diagram of a process for measuring suppression in the binocular vision of a patient, in accordance with some example embodiments.

FIG. 2 depicts a block diagram of an example of a process 200 for measuring suppression in the binocular vision of a patient. At the start of assessment for suppression, a clinician fits a patient with a computer-controlled stimuli presentation device, as in 205. As mentioned above, the computer-controlled stimuli presentation device may be 3D stereo shutter glasses, anaglyph glasses, polarized lenses, Wheatstone stereogram, head mounted displays, lenticular screens, or any other device or method that suitably presents different images to each eye. Once the patient is properly fitted, the clinician, in 210, presents slightly different stimuli to each eye of patient using computer-controlled stimuli presentation device. Then, in 215, the clinician asks the patient to report the stimulus observed. The patient reports what he or she observed using his or her binocular vision. These observations (e.g., reports) are provided to the controller so that an adaptive algorithm that is executed on the computer-controller may adjust the stimulus to present to the patient, and new stimuli are presented iteratively, in 220. The adaptive algorithm adjusts the stimulus, in 225, in response to the patient's observations until an estimate of the degree of suppression can be made by the clinician or computer-controller. The number of iterations is about 10 iterations of adjusting the stimulus until suppression can be assessed by the controller or the clinician.

Figure 3:
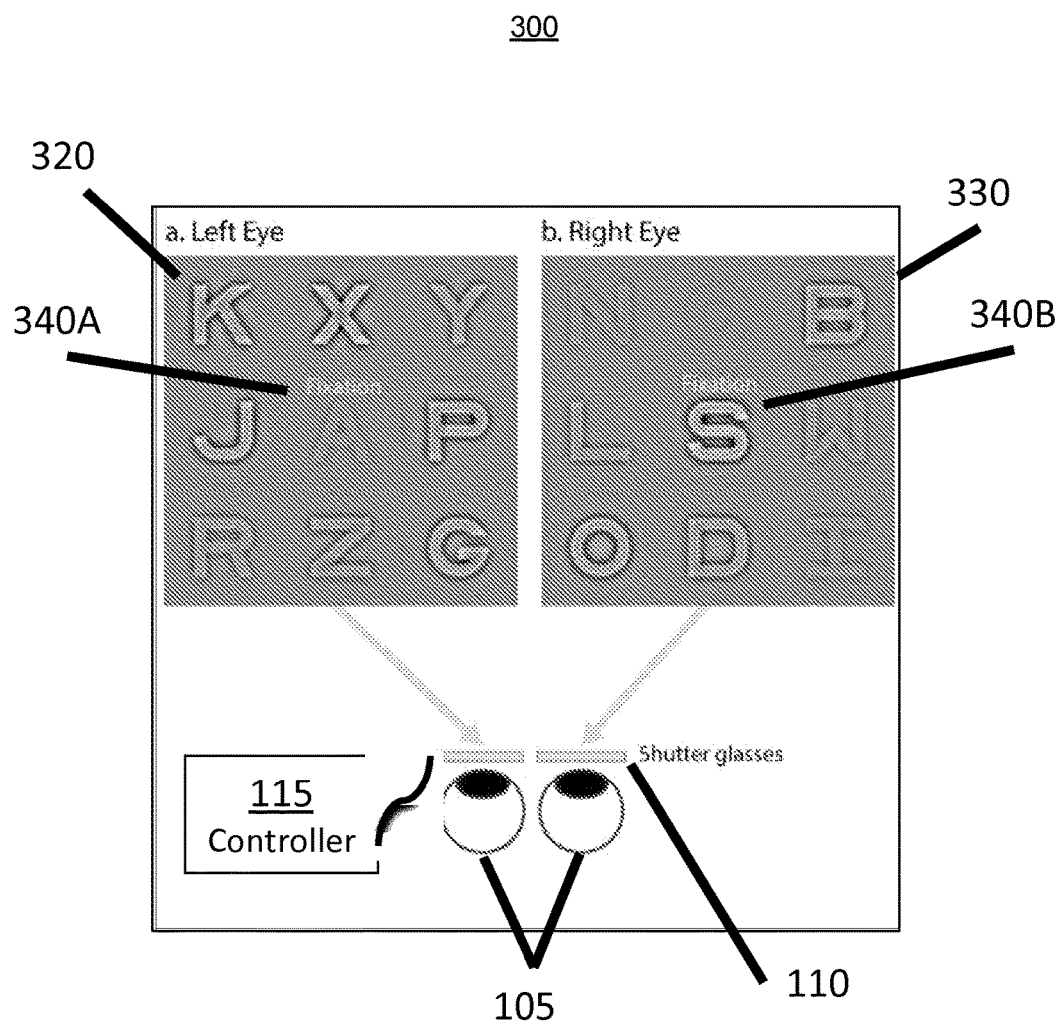
FIG. 3 depicts an example of a system for measuring suppression in the binocular vision of patient, in accordance with some example embodiments.

FIG. 3 depicts an example of a system 300 for measuring suppression in the binocular vision of patient. The system 300 is similar to that shown in FIG. 1A with a stimuli presentation device 110 that is placed before the patient's eyes 105, and a controller 115 that determines what is presented to the patient. The stimulus presented to the left eye 320 and to the right eye 330, includes Sloan letters in which the combined contrast of both letters is fixed and controlled by a computer associated with the controller. The difference is that the system shown in FIG. 3 measures regional suppression across the patient's visual field. The letters are arranged across the visual field to test suppression at different visual field locations. The visual field areas may be informed by extrinsic information, such as suspected diagnosis, retinal imaging data, subjective patient reports or questionnaires, and the like. Visual field areas can include about 10, 24, or 30 degrees diameter, which are similar to about 10-2, 24-2, or 30-2 Humphrey Visual Fields.

The patient reports to the clinician or the controller the letter identified as he or she reads from left to right, starting at the top row. The patient reads the letters while fixating the central letter 340A, 340B. Fixation is confirmed by eye-tracking technology. The inter-ocular contrasts across each position of the chart serve to sample different ratios to determine which eye perceives the letter at each ratio. As the controller presents charts in response to the patient's reports via a stimulus generating component and the stimuli presentation device 110, the inter-ocular contrast ratio of each letter is adaptively updated to determine the ratio at which the letter in each eye is reported with equal probability at each location. Thus, suppression is measured separately for each retinal location. To measure visual field suppression at different spatial frequency scales, the stimulus chart can be reproduced with bandpass filtered letters but at a different spatial frequency, and low (e.g., 0.5 c/deg) to high (12 c/deg) spatial frequencies, following the contrast sensitivity function.

Figure 4:
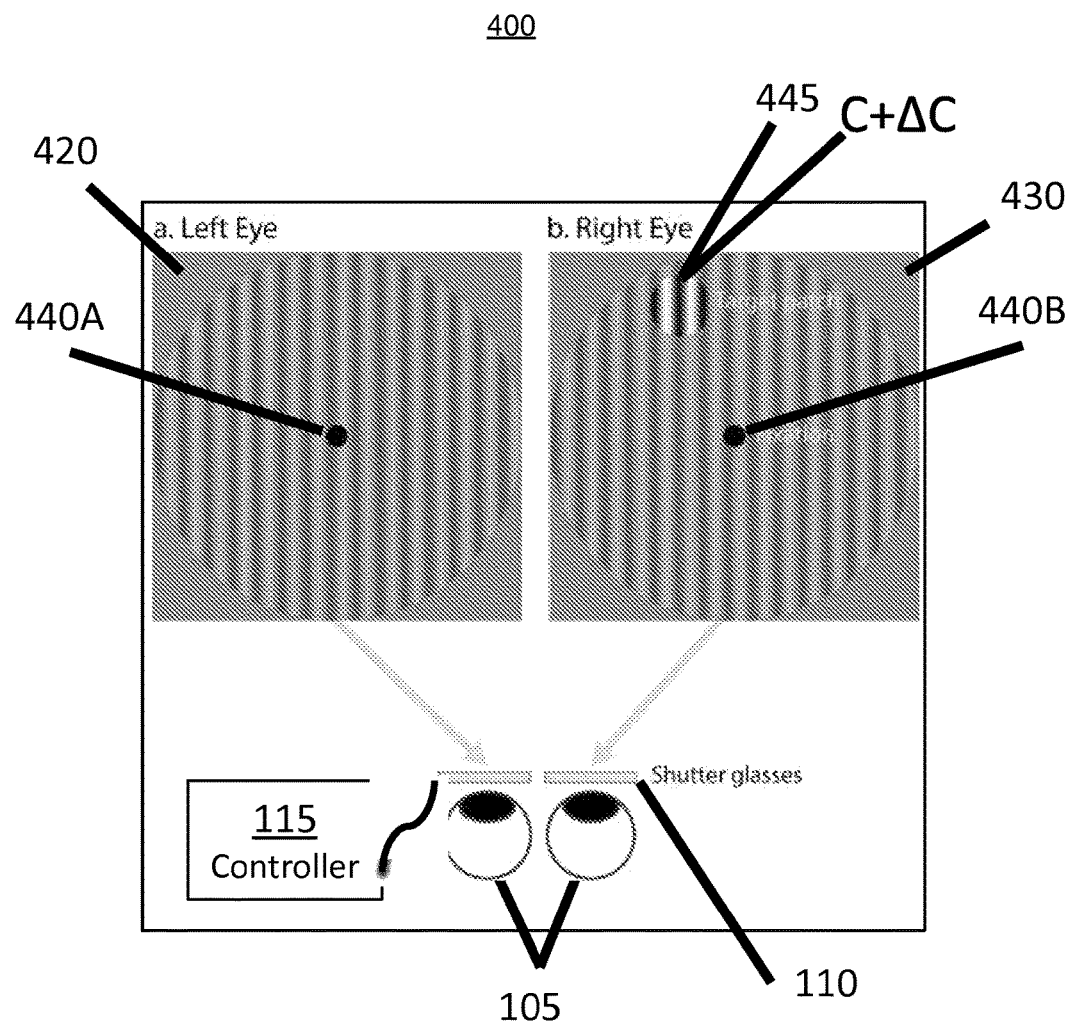
FIG. 4 depicts an example of a system for measuring both visual-field and spatial-frequency dependent suppression in the binocular vision of patient, in accordance with some example embodiments.

FIG. 4 depicts an an example of a system 400 for measuring both visual-field and spatial-frequency dependent suppression in the binocular vision of a patient. As with the systems of FIG. 1A and FIG. 3, the system 400 of FIG. 4 has a stimuli presentation device 110 that is placed before the patient's eyes 105, and a controller 115 that determines what is presented to the patient. The system of FIG. 4 may assess both visual-field and spatial frequency dependent suppression. In FIG. 4, the stimuli 420, 430 includes wide-field sinusoidal gratings with spatial-frequencies with diameters and spatial frequencies that may vary for each patient. Values for the diameter can include about 30 degrees (e.g., about 30-2 Humphrey Visual Field) and low (0.5 c/deg) to high (10 c/deg) spatial frequencies, following the contrast sensitivity function.

Each of the patient's eyes 105 is presented with an identical wide-field grating via the stimuli presentation device that is a pair of stereo-shutter glasses. Each iteration of stimuli presentation includes a localized contrast increment 445 that is applied to one of the eyes. In FIG. 4, the localized contrast increment 445, or test patch, is shown applied to the stimulus of the right eye 430. The size of the test patch 445 may vary according to the test location, the disease diagnosis, or upon extrinsic data such as retinal images or patient's answers to one or more questionnaires. Each test patch 445 is assessed in a random order. The patient's eyes 105 are fixated on central points 440A, 440B while he or she describes the presence of the test patch 445. Fixation of the patient's eyes 105 is confirmed by eye-tracking technology. The patient's descriptions are recorded by the clinician on a computer associated with the controller 115 or recorded directly by the controller 115, and inter-ocular threshold differences are accumulated across multiple iterations to determine spatial-frequency and visual-field dependent suppression thresholds.

In some example embodiments, an identical or nearly identical vertical grating, subtending 28 degrees of visual angle may be presented to the weak and strong eyes of an participant via 3D shutter glasses. The target patch may include a contrast increment ($\Delta C$) at 445 that may be presented to one of the eyes in random order. On a given trial, the target patch may appear in one of the two eyes and at one of 28 locations in the visual field in random order. Contrast-increment thresholds may be measured with a method of adjustment. The participant may be instructed to fixate on a central dot. The contrast may be increased until the central dot becomes distinguishable form the background. In some example embodiments, the contrast may be adjusted by the participant by using the up and down arrow keys on a computer keyboard or by using another computer input device.

In some example embodiments, the test stimulus may be a vertical sinusoidal grating (subtending 28 degrees of visual angle) with spatial frequency lying within a particular range. For example, the spatial frequency may be between 0.5 and 5 cycles per degree (cpd) at a viewing distance of 57 cm. The base contrast of the stimulus may be fixed at, for example, 30% while a contrast increment ($\Delta C$) may be applied to a circular patch (target patch). The target patch may be presented in one of 28 locations in the grating. An example target location is shown in FIG. 4 at 445. In some example embodiments, the size of the target patch may be 2° ($\leq 4.5°$ eccentricity), 2.5° ($4.5° < x \leq 8.25°$ eccentricity) and/or 3° ($8.25° < x \leq 13°$ eccentricity) in diameter depending on the eccentricity of the target location in the visual field with respect to the fovea, indicated by the black fixation dot 440A/440B in FIG. 4.

In some example embodiments, suppression may be defined as a difference in contrast-increment thresholds between the two eyes when a contrast increment (ΔC) is presented to one of the eyes while an identical stimulus with a pedestal contrast (C) was presented to both eyes. In the example of FIG. 4, an identical vertical pedestal grating may be presented to the weak and strong eyes of an observer via the 3D shutter glasses while a target patch containing a contrast increment (ΔC) may be presented only to one eye. For a given trial, the target patch may appear in one of the two eyes and at one of 28 locations in the visual field. The arrangement of the target locations may be circular and symmetric with respect to the origin. In some example embodiments, there may be 12 locations for the target patch in the visual field where eccentricity is equal to or less than 4.5°, and 16 locations of which eccentricity is greater than 4.5° and equal to or less than 13°. The target locations may be approximately evenly distributed across the visual field and adjusted in size, to respect cortical magnification. The presentation sequence of the target in each eye and visual field location may be randomized across trials. In this way, the participant may not know which eye or test location for the next target. Data for the two spatial frequencies (0.5 and 5 c/deg) may be collected in different runs, in random order across participants. Other spatial frequencies, target patch shapes, target patch locations, target patch angular range, and/or target patch sizes may also be used.

Figure 5:
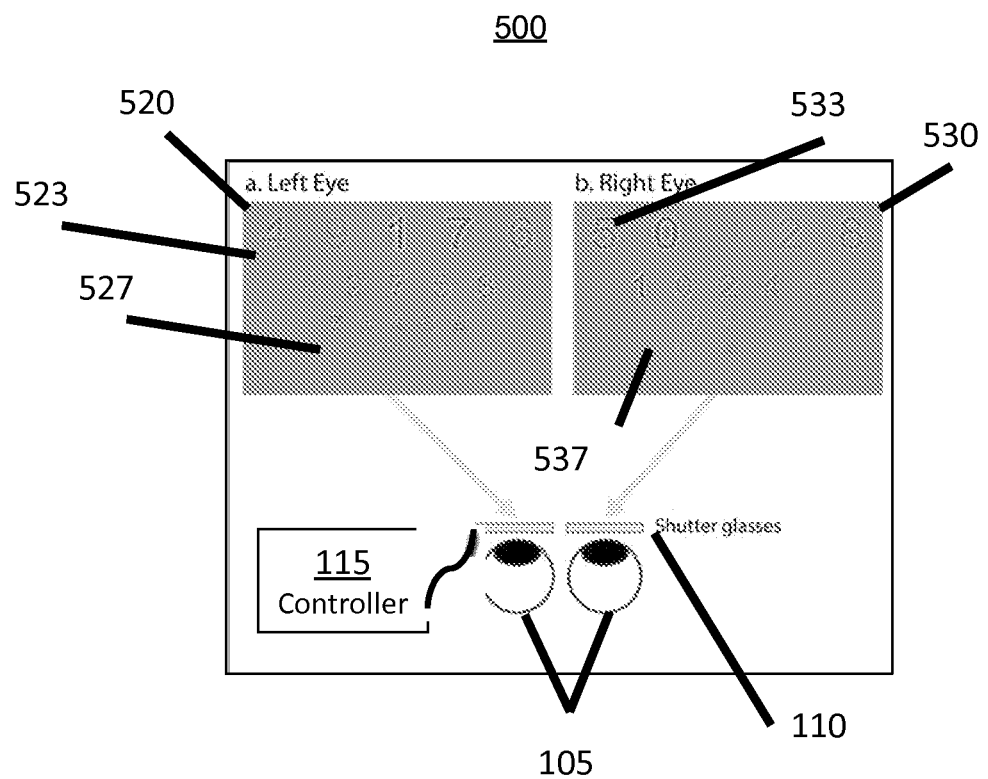
FIG. 5 depicts an example of a system for measuring scale dependent suppression in the binocular vision of patient that employs numbers, in accordance with some example embodiments.
Figure 6:
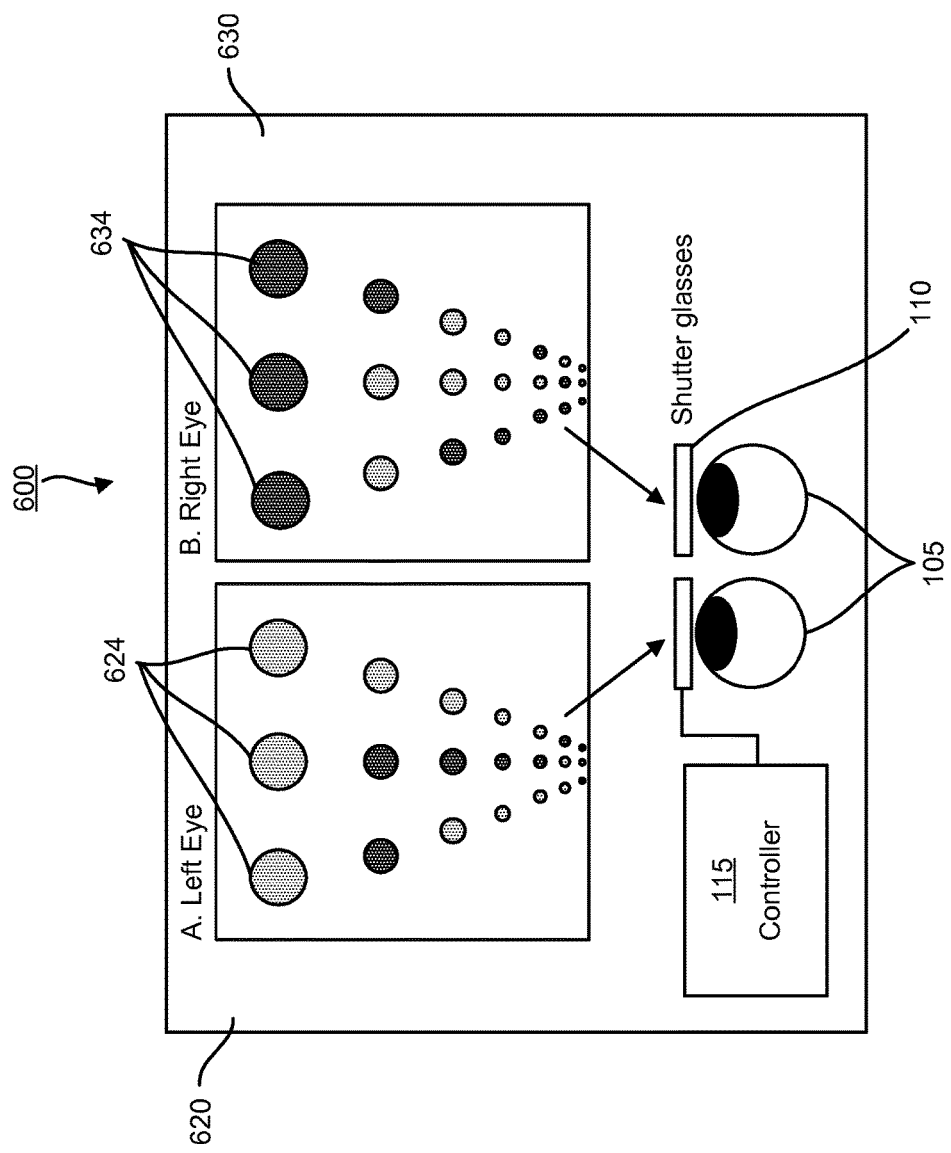
FIG. 6 depicts an example of a system for measuring scale dependent suppression in the binocular vision of patient that employs colored targets, in accordance with some example embodiments.

FIGS. 5 and 6 depict systems for measuring suppression in patients who may not be able to identify letters in stimuli. FIG. 5 depicts an example of a system 500 for measuring scale dependent suppression in the binocular vision of patient that employs stimuli 520, 530 with bandpass filtered numbers 523, 527, 533, 537. In FIG. 5 the interocular ratio of contrast is adjusted by the controller 115 based on the reports of the patient. In this manner, the system 500 finds the effective level that causes the patient to report the number in each eye with equal frequency.

FIG. 6 depicts an example of a system 600 for measuring scale dependent suppression in the binocular vision of patient that employs stimuli 620, 630 with colored targets 624, 634. Although FIG. 6 shows targets 624, 634 as shaded gray, the targets may be colored. For example, targets 624 may be green, and/or targets 634 may be red. Targets 624, 634 may also be any other color as well. Each spot of color in the stimuli 620, 630 of the system 600 shown in FIG. 6 is adjusted by the controller 115 until the patient reports the color of each eye with equal frequency.

Figure 7:
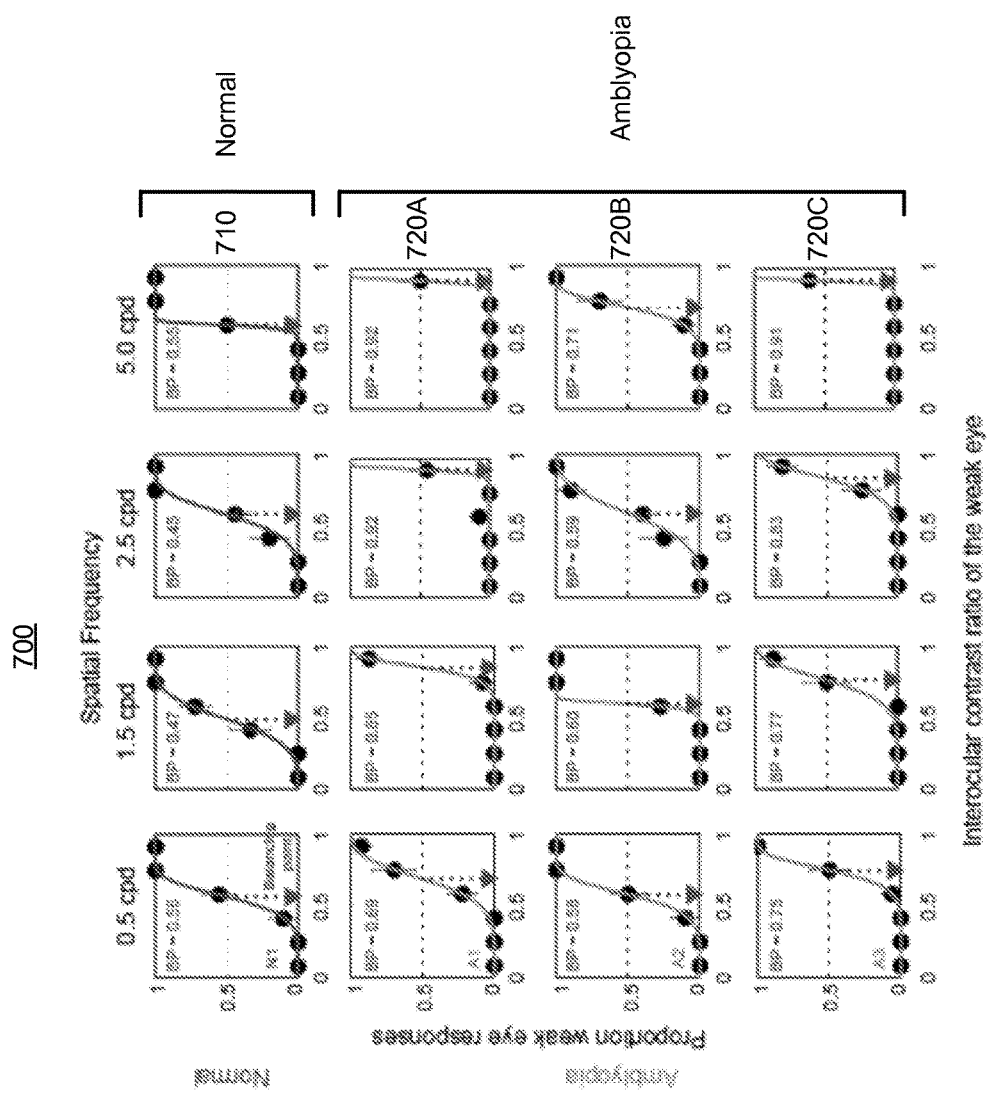
FIG. 7 depicts examples of graphs showing proportion of weak eye responses as a function of interocular contrast ratio and spatial frequency, in accordance with some example embodiments.

FIG. 7 depicts example responses consistent with reliance on the weaker eye ("weak eye responses") that are plotted against interocular contrast ratio. Each row in FIG. 7 shows data from an individual participant. Each graph in FIG. 7 shows a proportion of weak eye responses as a function of interocular contrast ratio. Each graph corresponds to a spatial frequency with the graphs arranged from lower spatial frequency to higher spatial frequency for each row from left to right. The top row 710 corresponds to a participant with normal vision and the bottom three rows 720A, 720B, 720C correspond to three participants with amblyopia. Each column corresponds to a different spatial frequency from 0.5, 1.5, 2.5 and 5 c/deg. In some example embodiments, the balance point may be determined by fitting the data using a Weibull function and finding the contrast ratio corresponding to 0.5 proportion of weak eye responses. In some example embodiments, the above described model may fit with r2 values of 0.989 to 0.999 (mean 0.994±0.003), indicating that about 99% of variance is accounted for by the model.

In the example of FIG. 7, the solid lines in each graph in rows 710, 720A-C show the best fit of the data to the forgoing process. The dotted arrow lines indicate the determined balance points. Row 710 corresponds to a participant with normal vision. Row 720A corresponds to a participant with strabismic amblyopia. Row 720B corresponds to a participant with anisometropic amblyopia. Row 710 corresponds to a participant with anisometropic amblyopia.

In some example embodiments, the balance points of participants with amblyopia may increase with increasing spatial frequency. For example, the balance point may increase with increasing frequency as represented by a rightward shift of the psychometric function. For example, the balance point of the weak eye at row 720A increased from 0.69 at 0.5 c/deg. to 0.92 at 5 c/deg. This may indicate, for example, that for a low spatial frequency, 69% contrast is required for the weak eye to match 31% contrast in the strong eye while for a high spatial frequency 92% of contrast is needed for the weak eye to match 8% contrast in the strong eye. This substantially higher balance point may be observed in participants with amblyopia suggesting that input from the weak eye is attenuated or suppressed by the strong eye under conditions of suprathreshold perception. The suppression may be more pronounced at higher spatial frequencies. The balance points of normally sighted observers may be close to a value of 0.5, indicating that the input signals from the two eyes may be treated approximately equally and in a manner that is largely independent of spatial frequency.

Figure 8:
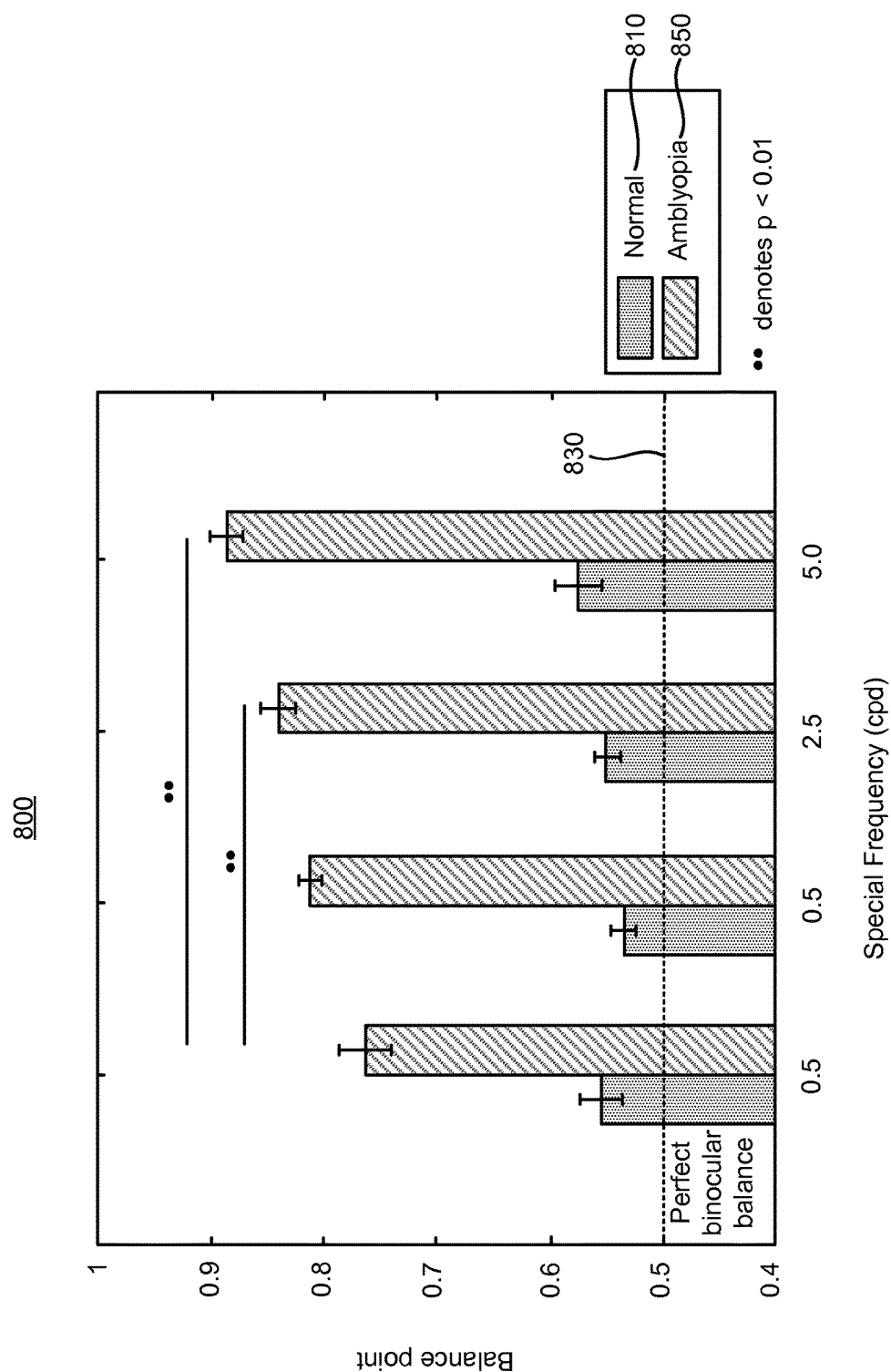
FIG. 8 depicts an example of a graph of balance points as a function spatial frequency for normal and amblyopic patients, in accordance with some example embodiments.

In accordance with some example embodiments, FIG. 8 depicts mean balance points as a function of spatial frequency for participants with amblyopia 820 and normal vision 810. The dotted line 830 indicates a proportion of weak-eye responses equal to 0.5, indicating balanced contrast perception between the two eyes, i.e. no interocular suppression. Consistent with individual data (see, for example, FIG. 7), across spatial frequencies the balance points for the amblyopic group (0.80±0.02) may be higher than for the normal control group (0.55±0.01). Error bars in FIG. 8 represent ±1 Standard Errors of the Mean (SEM).

Although some of the drawings show examples of results, other results may be obtained as well.

A two-way repeated measures ANOVA may support a significant main effect of subject group ($F_{(3, 30)}$=3.48, p=0.028) on balance point. Balance points of an amblyopia group may differ across different spatial frequencies ($F_{(3, 12)}$=6.26, p=0.008) while that of a normal group may remain constant across different spatial frequencies ($F_{(3, 18)}$=0.62, p=0.601). Tukey's HSD pairwise comparison test may further reveal that the balance point of the spatial frequency of 0.5 c/deg. may be different from either that of 2.5 or 5 c/deg. (all p<0.01), which may suggest that the balance point increases with spatial frequency in amblyopic observers. The average balance point of the normal control group (0.55±0.01) may be significantly different from a value of 0.5 ($t_{(6)}$=5.93, p=0.001), which may indicate mild eye dominance in normally-sighted individuals.

The subject matter described herein may be embodied in systems, apparatus, methods, and/or articles depending on the desired configuration. For example, the controllers of a system for quantifying inter-ocular suppression in binocular vision impairment (or one or more components therein) and/or the processes described herein can be implemented using one or more of the following: a processor executing program code, an application-specific integrated circuit (ASIC), a digital signal processor (DSP), an embedded processor, a field programmable gate array (FPGA), and/or combinations thereof. These various implementations may include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device. These computer programs (also known as programs, software, software applications, applications, components, program code, or code) include machine instructions for a programmable processor, and may be implemented in a high-level procedural and/or object-oriented programming language, and/or in assembly/machine language. As used herein, the phrase "machine-readable medium" refers to any computer program product, computer-readable medium, apparatus and/or device (e.g., magnetic discs, optical disks, memory, Programmable Logic Devices (PLDs)) used to provide machine instructions and/or data to a programmable processor, including a machine-readable medium that receives machine instructions. Similarly, systems are also described herein that may include a processor and a memory coupled to the processor. The memory may include one or more programs that cause the processor to perform one or more of the operations described herein.

Although a few variations have been described in detail above, other modifications or additions are possible. In particular, further features and/or variations may be provided in addition to those set forth herein. For example, the implementations described above may be directed to various combinations and subcombinations of the disclosed features and/or combinations and subcombinations of several further features disclosed above. In addition, the logic flow depicted in the accompanying figures and/or described herein does not require the particular order shown, or sequential order, to achieve desirable results. In various example implementations, the methods (or processes) can be accomplished on mobile station/mobile device side or on the server side or in any shared way between server and user equipment/mobile device with actions being performed on both sides. The phrases "based on" and "based on at least" are used interchangeably herein. Other implementations may be within the scope of the following claims.

What is claimed is:

1. A system for quantifying suppression in binocular vision of a patient, the system comprising:
    a stimuli presentation device configured to present stimuli comprising a distinct stimulus for each eye of the patient, the distinct stimulus including a first stimulus for a right eye and a second stimulus for a left eye; and
    a controller, operably connected to the stimuli presentation device, the controller comprising:
        a computer comprising an interface configured to accept input from a clinician, a patient, or both,
        an adaptive algorithm executed on the computer, the adaptive algorithm configured to accept a report describing what the patient sees when presented with the stimuli and calculate adjustments to the stimuli to be presented in a next iteration of stimuli, and
        a stimulus generating component configured to provide the next iteration of stimuli to the patient via the stimuli presentation device,
    wherein the first stimulus for the right eye includes a first feature and a second feature, the first feature including a first contrast value, the second feature including a second contrast value;
    wherein the second stimulus for the left eye includes a third feature and a fourth feature, the third feature corresponding to the first feature and including a third contrast value, the fourth feature corresponding to the second feature and including a fourth contrast value;
    wherein a sum of the first contrast value and the third contrast value equals a fixed amount;
    wherein a sum of the second contrast value and the fourth contrast value equals the fixed amount.

2. The system of claim 1, wherein the stimuli presentation device comprises 3D stereo shutter glasses, anaglyph glasses, polarized lenses, a Wheatstone stereogram, head mounted displays, and/or lenticular screens.

3. The system of claim 1, wherein the system is configured to measure scale dependent suppression in the binocular vision of the patient.

4. The system of claim 3, wherein the stimuli comprise bandpass filtered Sloan letters laid out in a manner comprising multiple rows of letters, each row of decreasing letter size, and each row having multiple letter, wherein each letter in a row is distinct and having a different amount of contrast.

5. The system of claim 4, wherein each distinct stimulus for each eye of the patient has the same number of rows of letters and columns of letters, wherein a letter on a right eye stimulus corresponds to a letter on a left eye stimulus in a similar position, further wherein the corresponding letters have a combined contrast that is the fixed amount.

6. The system of claim 3, wherein the Sloan letters of the stimuli comprise peak spatial-frequencies of 0.5 to 10 cycles per degree.

7. The system of claim 3, wherein the Sloan letters create a pattern that covers a main area of a contrast sensitivity function.

8. The system of claim 1, wherein the system is configured to measure suppression in the binocular vision of the patient while each eye of the patient is fixated on a spot on the distinct stimulus presented to each eye.

9. The system of claim 1, wherein the system is configured to measure both visual-field and spatial-frequency dependent suppression in the binocular vision of the patient.

10. The system of claim 1, wherein the stimuli comprise numbers or colored dots.

11. The system of claim 1, wherein the stimulus generating component comprises program code executed on the computer.

12. A method comprising:
    presenting, via a computer controller and a stimuli presentation device, stimuli to a patient, the stimuli comprising a distinct stimulus for each eye of the patient, the distinct stimulus including a first stimulus for a right eye and a second stimulus for a left eye;
    accepting, via the computer controller, reports comprising observations from the patient regarding the stimuli;
    creating an adjusted stimuli via an adaptive algorithm executed on the computer controller, the adaptive algorithm using the reports as input; and
    presenting to the patient the adjusted stimuli via a stimulus generating component of the computer controller and the stimuli presentation device;
    wherein the first stimulus for the right eye includes a first feature and a second feature, the first feature including a first contrast value, the second feature including a second contrast value;

wherein the second stimulus for the left eye includes a third feature and a fourth feature, the third feature corresponding to the first feature and including a third contrast value, the fourth feature corresponding to the second feature and including a fourth contrast value;
wherein a sum of the first contrast value and the third contrast value equals a fixed amount;
wherein a sum of the second contrast value and the fourth contrast value equals the fixed amount.

13. The method of claim 12, further comprising evaluating the reports to determine whether suppression in binocular vision of the patient can be quantified.

14. The method of claim 12, further comprising quantifying suppression in binocular vision of the patient.

15. The method of claim 12, wherein the stimuli comprise bandpass filtered Sloan letters, numbers, or colored dots.

16. The method of claim 15, wherein the first feature, the second feature, the third feature and the fourth feature comprise the bandpass filtered Sloan letters, numbers, or colored dots.

17. The method of claim 16, wherein the first stimulus and the second stimulus further comprise additional corresponding features, each additional feature has a contrast value, further wherein a sum of the additional contrast values for corresponding additional features equals the fixed amount, the fixed amount being the same for each pair of corresponding features.

18. The method of claim 12, wherein the stimulus generating component comprises program code executed on the computer controller.

19. The method of claim 12, wherein the stimuli presentation device comprises 3D stereo shutter glasses, anaglyph glasses, polarized lenses, a Wheatstone stereogram, head mounted displays, and/or lenticular screens.

20. A non-transitory computer-readable medium encoded with instructions that, when executed by at least one processor, cause operations comprising:
presenting, via a computer controller and a stimuli presentation device, stimuli to a patient, the stimuli comprising a distinct stimulus for each eye of the patient, the distinct stimulus including a first stimulus for a right eye and a second stimulus for a left eye;
accepting, via the computer controller, reports comprising observations from the patient regarding the stimuli;
creating an adjusted stimuli via an adaptive algorithm executed on the computer controller, the adaptive algorithm using the reports as input; and
presenting to the patient the adjusted stimuli via a stimulus generating component of the computer controller and the stimuli presentation device;
wherein the first stimulus for the right eye includes a first feature and a second feature, the first feature including a first contrast value, the second feature including a second contrast value;
wherein the second stimulus for the left eye includes a third feature and a fourth feature, the third feature corresponding to the first feature and including a third contrast value, the fourth feature corresponding to the second feature and including a fourth contrast value;
wherein a sum of the first contrast value and the third contrast value equals a fixed amount;
wherein a sum of the second contrast value and the fourth contrast value equals the fixed amount.

21. An apparatus comprising:
means for presenting, via a computer controller and a stimuli presentation device, stimuli to a patient, the stimuli comprising a distinct stimulus for each eye of the patient, the distinct stimulus including a first stimulus for a right eye and a second stimulus for a left eye;
means for accepting, via the computer controller, reports comprising observations from the patient regarding the stimuli;
means for creating an adjusted stimuli via an adaptive algorithm executed on the computer controller, the adaptive algorithm using the reports as input; and
means for presenting to the patient the adjusted stimuli via a stimulus generating component of the computer controller and the stimuli presentation device;
wherein the first stimulus for the right eye includes a first feature and a second feature, the first feature including a first contrast value, the second feature including a second contrast value;
wherein the second stimulus for the left eye includes a third feature and a fourth feature, the third feature corresponding to the first feature and including a third contrast value, the fourth feature corresponding to the second feature and including a fourth contrast value;
wherein a sum of the first contrast value and the third contrast value equals a fixed amount;
wherein a sum of the second contrast value and the fourth contrast value equals the fixed amount.

22. The apparatus of claim 21, further comprising evaluating the reports to determine whether suppression in binocular vision of the patient can be quantified.

23. The apparatus of claim 21, further comprising quantifying suppression in binocular vision of the patient.

24. The apparatus of claim 21, wherein the stimuli comprise bandpass filtered Sloan letters, numbers, or colored dots.

25. The apparatus of claim 24, wherein the first feature, the second feature, the third feature and the fourth feature comprise the bandpass filtered Sloan letters, numbers, or colored dots.

26. The apparatus of claim 25, wherein the first stimulus and the second stimulus further comprise additional corresponding features, each additional feature has a contrast value, further wherein a sum of the additional contrast values for corresponding additional features equals the fixed amount, the fixed amount being the same for each pair of corresponding features.

* * * * *